United States Patent
Kohro et al.

(10) Patent No.: US 8,183,306 B2
(45) Date of Patent: May 22, 2012

(54) TWO-PASTE TYPE DENTAL SELF-ADHESIVE RESIN CEMENT

(75) Inventors: Yoshiaki Kohro, Kyoto (JP); Hisaki Tanaka, Kyoto (JP); Keisuke Torii, Kyoto (JP); Toshiyuki Nakatsuka, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 266 days.

(21) Appl. No.: 12/318,099

(22) Filed: Dec. 22, 2008

(65) Prior Publication Data

US 2010/0010115 A1   Jan. 14, 2010

(30) Foreign Application Priority Data

Jul. 8, 2008 (JP) ................................ 2008-177989

(51) Int. Cl.
*A61K 6/08* (2006.01)
(52) U.S. Cl. ........................................................ 523/116
(58) Field of Classification Search ................... 523/116
See application file for complete search history.

(56) References Cited

U.S. PATENT DOCUMENTS

2007/0203257 A1 * 8/2007 Qian ............................. 523/116
2009/0048366 A1 * 2/2009 Torii et al. ..................... 523/116

FOREIGN PATENT DOCUMENTS

WO   WO 2007088628 A1 *  8/2007

* cited by examiner

*Primary Examiner* — Mark Eashoo
*Assistant Examiner* — David Karst
(74) *Attorney, Agent, or Firm* — Wenderoth, Lind & Ponack, L.L.P.

(57) ABSTRACT

The present invention provides a dental self-adhesive resin cement having clinically-acceptable adherability for various adherends without pre-treatment with primers. Specifically, there is provided the dental self-adhesive composite resin cement comprising:
(a) a radical polymerizable monomer,
(b) a polymerizable monomer having a phosphonic acid group and/or a phosphoric acid ester group,
(c) a polymerizable monomer having a dibasic acid carboxyl group,
(d) a filler, and
(e) a polymerization catalyst.

1 Claim, No Drawings

TWO-PASTE TYPE DENTAL SELF-ADHESIVE RESIN CEMENT

This application is based on application No. 2008-177989 filed in Japan, the contents of which are hereby incorporated by reference.

FIELD OF THE INVENTION

The present invention relates to a self-adhesive resin cement. More specifically, the present invention relates to a resin cement to which adherability for each of various adherends is imparted, in the case where a dental prosthetic restoration composition consisting of ceramic, composite resins or metal materials is adhered to a base such as a biological hard tissue, particularly enamel or dentin of natural teeth, without pre-treatment with a primer for teeth, porcelain, ceramic or metal materials conventionally used. Moreover, the present invention relates to a composite type self-adhesive resin cement, which comprises a resin cement paste having the excellent physical property.

BACKGROUND OF THE INVENTION

A resin cement generally used in the dental field is categorized into a composite type and a poly(methyl methacrylate) (PMMA) type, but the present invention is limited to the composite type excellent in the physical property of the resin cement itself. In recent years, the resin cement is highly required as an adhesive for a dental prosthetic restoration composition exhibiting the aesthetic property, and the composition contains a filler consisting of an organic, inorganic and/or organic-inorganic composite material, and a polymerizable monomer or oligomer. In the restoration composition, a filling ratio of the filler is approximately not less than 50% by weight in order to achieve a high material strength. In addition, in order to polymerize and cure the resin cement even at a portion where light does not reach, a dual-cure type of the resin cement has been mainly used, which has the chemical polymerization function in addition to the photopolymerization function.

For restoring teeth which have underwent a relatively large damage due to dental caries or the like, a procedure is generally used, in which a crown, a bridge, an inlay, an onlay, etc. which is made of ceramic, composite resins or metal materials is adhered on the damaged portion with the resin cement. In such the case, a pre-treatment agent, so called a primer, is used, in order to strengthen adherability of the resin cement to a dental hard tissue. Sufficient adherability and a material strength are required for such the resin cement. Otherwise, not only the dental restorative composition may be dropped from the teeth during a long period use under severe oral environment, but also a gap may be produced at an interface between the resin cement and the teeth, and bacteria may invade therefrom and adversely effect on dental pulp.

The dental hard tissue is composed of enamel and dentin, and adhesion of the resin cement to both of them is clinically required. The primer for pre-treating a tooth surface has been conventionally used prior to application of the resin cement for enhancing adherability. Such the primer demineralizes the tooth surface to make it rough, and facilitating infiltration of the resin cement into a fine rough surface. An adhesion mechanism that, thereafter, the resin cement is cured by chemical polymerization or photopolymerization is considered.

On the other hand, as the conventional resin cement, a powder-liquid type has been used, but a resin cement which is used by mixing two pre-pasted compositions has been highly required in order to avoid a cumbersome procedure of mixing the powder and the liquid. Such the procedure of mixing the pastes reduces a mixing time and a difference between persons as compared with the procedure of mixing the powder and the liquid and, therefore, is a preferable type for clinicians. Moreover, in addition to by photopolymerization, the polymerization curing function by chemical polymerization, i.e. the dual cure polymerization curing function, is required for such the resin cement, so that it may be used for a high light-transmittable prosthetic restoration composition such as dental porcelain, in addition to a low light-transmittable prosthetic restoration composition such as a dental alloy.

However, prior to adhesion with the resin cement, each adherend of teeth, ceramic, composite resins and metal materials should be treated with an exclusive primer for each of various adherends in advance. Clinically, a simple adhesion procedure is desired, which does not require a primer treatment for such various adherends.

Japanese Patent Publication No. 2006-512466A discloses a self-adhesive resin cement which does not require the primer, that is a polymerizable composite material comprising at least one multifunctional monomer containing an acid in a concentration range of about 10-85% by weight, a non-reactive filler in a concentration range of about 1-80% by weight, a polymerization system in a concentration range of about 1.5-25% by weight, and water in a concentration range of about 0.1-25% by weight. However, since such the composition uses a single acidic monomer, sufficient adherability cannot be attained for both of inorganic component-rich enamel and organic component- and water-rich dentin.

European Patent Publication No. 1502569 A1 discloses a method for providing a two paste self-adhesive dental composition comprising a polymerizable monomer having an acidic group, a polymerizable monomer having no acidic monomer, a fine particulate filler, a reducing agent and an oxidizing agent. Specifically, it discloses that a ratio of a paste having a greater content of the polymerizable monomer having an acidic group and a paste having a smaller content of the monomer having an acidic group is greater than 1:1. When a ratio of the pastes is changed, an apparatus for feeding the paste becomes troublesome.

Japanese Patent Publication No. 2000-53518A and International Publication No. WO 02/092021A1 disclose a self-adhesive dental cement composition consisting of a liquid and a powder, but the resin cement consisting of the liquid and the powder, i.e. a powder-liquid type resin cement, is inferior in manipulability upon mixing as compared with a paste-and-paste type resin cement.

Japanese Patent Publication No. 2005-65902A discloses a dental adhesive composition comprising, as an essential adhesive component, a carboxylic acid compound having one (meth)acryloyl group and one carboxyl group which are bound to an aromatic group as a polymerizable monomer containing a particular carboxylic acid group. However, such the polymerizable monomer having a carboxylic acid group cannot impart sufficient clinically acceptable adherability for enamel.

International Patent Application No. PCT/JP2006/301845 discloses a resin cement comprising a metal salt of barbituric acid, an organic peroxide and an amine as a curing agent. However, with this resin cement, it is necessary that the teeth are pre-treated with an exclusive primer.

SUMMARY OF THE INVENTION

The present invention was done in light of such current status, and an object thereof is to provide a self-adhesive dental resin cement having clinically acceptable adherability for various adherends having different properties such as teeth, both of enamel and dentin, ceramic such as zirconia, alumina, etc., porcelain and metal materials, without pretreatment with a primer.

The present inventors have been intensively studied a resin cement paste which does not require the primer and, as a result, found that a two-paste type dental self-adhesive composite resin cement comprising following components:

(a) a radical polymerizable monomer, (b) a polymerizable monomer having a phosphonic acid group and/or a phosphoric acid ester group, (c) a polymerizable monomer having a dibasic acid carboxyl group, (d) a filler, and (e) a polymerization catalyst and is substantially free from water, can solve problems in the prior art, and can impart strong adherability for a biological hard tissue, particularly a base of enamel and dentin, ceramic, composite resins or metal materials, without treatment with a primer, which resulted in completion of the present invention. That is, it is found that, as a polymerizable monomer having an acidic group for promoting adhesion, referred to as a adhesive monomer, in the case where a polymerizable monomer having a functional group of phosphonic acid and phosphoric acid ester and a polymerizable monomer having a dibasic acid carboxyl group are contained in combination, more advantageous adhesion, i.e. an synergistic effect, is exhibited as compared with the case where each of them is individually contained, which resulted in completion of the present invention.

Specifically, the present invention provides:

(1) A two-paste type dental self-adhesive composite resin cement, comprising:

(a) a radical polymerizable monomer, (b) a polymerizable monomer having a phosphonic acid group and/or a phosphoric acid ester group, (c) a polymerizable monomer having a dibasic acid carboxyl group, (d) a filler, and (e) a polymerization catalyst;

(2) The two-paste type dental self-adhesive composite resin cement according to aforementioned (1), the cement consisting of a first paste and a second paste, wherein, the first paste comprises:

(a) a radical polymerizable monomer, (d) a filler, and (e)-(1) a polymerization accelerator, and the second paste comprises:

(a) a radical polymerizable monomer, (b) a polymerizable monomer having a phosphonic acid group and/or a phosphoric acid ester group, (c) a polymerizable monomer having a dibasic acid carboxyl group, (d) a filler, and (e)-(2) a polymerization initiator, and wherein both of the pastes are free from water;

(3) The two-paste type dental self-adhesive composite resin cement according to aforementioned (1) or (2), wherein the component (b), a polymerizable monomer having a phosphonic acid group and/or a phosphoric acid ester group is the monomer having a phosphonic acid group represented by the general formula [I]:

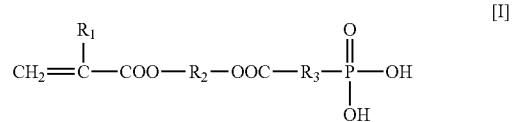

wherein $R_1$ is a hydrogen atom or a methyl group, $R_2$ is an alkylene group of the carbon atom number of 5-10, and $R_3$ is an alkylene group of the carbon atom number of 1-6;

(4) The two-paste type dental self-adhesive composite resin cement according to aforementioned (2) or (3), wherein the component (e)-(1) of the first paste is an alkali metal salt or an alkaline earth metal salt of barbituric acid and/or aromatic secondary or tertiary amine;

(5) The two-paste type dental self-adhesive composite resin cement according to any one of aforementioned (2) to (4), wherein the component (e)-(2) of the second paste is a chemical polymerization initiator and/or a photopolymerization initiator;

(6) The two-paste type dental self-adhesive composite resin cement according to any one of aforementioned (1) to (5), which exhibits an effective shear bond strength or tensile bond strength for all of teeth, dental porcelain, zirconia, composite resins and gold alloys;

(7) The two-paste type dental self-adhesive composite resin cement according to aforementioned (6), further comprising a component (f), a shelf time stabilizer;

(8) A two-paste type dental self-adhesive composite resin cement consisting of a first paste and a second paste, which exhibits an effective shear bond strength or tensile bond strength for all of teeth, dental porcelain, zirconia, composite resins and gold alloys, wherein, the first paste comprises, on a basis of 50% by weight of the first paste:

(a) 8.0-22.5% by weight of a radical polymerizable monomer, (d) 27.45-40.0% by weight of a filler, and (e)-(1) 0.025-2.0% by weight of an alkali metal salt or an alkaline earth metal salt of barbituric acid and/or 0.025-0.5% by weight of aromatic secondary or tertiary amine, and the second paste comprises, on a basis of 50% by weight of the second paste:

(a) 5.0-22.5% by weight of a radical polymerization monomer, (b) 0.05-3.0% by weight of a polymerizable monomer having a phosphonic acid group and/or a phosphoric acid ester group, (c) 0.05-3.0% by weight of a polymerizable monomer having a dibasic acid carboxyl group, (d) 27.3-40.0% by weight of a filler, and (e)-(2) 0.1-1.0% by weight of a chemical polymerization initiator and/or a photopolymerization initiator, and wherein both of the pastes are free from water.

The two-paste type dental self-adhesive composite resin cement of the present invention has sufficient adherability for the teeth such as enamel, dentin, etc., dental ceramic, composite resins and metal materials.

As the component (a), a radical polymerizable monomer, used in the two-paste type dental self-adhesive composite resin cement of the present invention (hereinafter, referred to as "resin cement"), all of radical polymerizable monomers that do not contain an acid group may be used, and examples include (meth)acrylic acid ester derivatives, alkylene glycol di(meth)acrylates, alkyl di(meth)acrylates, epoxy di(meth)

acrylates, bisphenol A-alkyl di(meth)acrylates, urethane di(meth)acrylates, urethane tri(meth)acrylates, urethane tetra(meth)acrylates, hydroxyalkyl(meth)acrylates, (meth)acrylates having a silicon group, (meth)acrylates having a —SH or —S—S— group, and styrene derivatives. Specifically, example includes methyl(meth)acrylate, ethyl(meth)acrylate, ethyleneglycol di(meth)acrylate, triethyleneglycol di(meth)acrylate, di-2-methacryloyloxyethyl-2,2,4-trimethylhexamethylene dicarbamate, 2,2'-bis[4-(3-(meth)acryloyloxy-2-hydroxypropoxy)phenyl]propane, di(meth)acryloxyisophorone dicarbamate, 2-hydroxyethyl(meth)acrylate, 6-hydroxyhexyl (meth)acrylate, 2-hydroxypropyl(meth)acrylate, glycerol di(meth)acrylate, and γ-methacryloxypropyltrimethoxysilane, etc. A particularly suitable radical polymerizable monomer includes ethyleneglycol di(meth)acrylate, triethyleneglycol di(meth)acrylate, hexamethyleneglycol di(meth)acrylate, 1,6-hexane di(meth)acrylate, di(meth)acryloxyethyl-2,2,4-trimethylhexamethylene diurethane, di(meth)acryloxyisophorone diurethane, 2,2'-bis[4-(3-(meth)-acryloyloxy-2-hydroxypropoxy)phenyl]propane, 2-hydroxyethyl(meth)acrylate, 2-hydroxypropyl(meth)acrylate, glycerol di(meth)acrylate, etc. Among them, ethyleneglycol di(meth)acrylate, triethyleneglycol di(meth)acrylate, di-2-methacryloyloxyethyl-2,2,4-trimethylhexamethylene dicarbamate, 2,2,-bis[4-(3-(meth)acryloyloxy-2-hydroxypropoxy)phenyl]propane and 2-hydroxyethyl(meth)acrylate are particularly suitable. These radical polymerizable monomers may be used alone or by mixing two or more of them.

An amount of the component (a), the radical polymerizable monomer, in the resin cement of the present invention is usually 13.0-45.0% by weight, preferably 15.0-40.0% by weight, more preferably 20.0-35.0% by weight, based on a total amount of the resin cement of combining two pastes. When the amount is less than 13.0% by weight, then a viscosity of the paste becomes too high, whereas when it is greater than 45.0% by weight, then a viscosity of the paste becomes too low and, as the result, the paste property suitable for use as the resin cement cannot be obtained.

Examples of the component (b), a polymerizable monomer having a phosphonic acid group and/or a phosphoric acid ester group, used in the resin cement of the present invention include a polymerizable monomer represented by the general formula [I]:

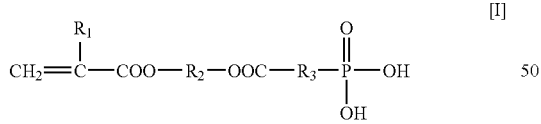

(wherein $R_1$ is a hydrogen atom or a methyl group, $R_2$ is an alkylene group having the carbon atom number of 5 to 10, and $R_3$ is an alkylene group having the carbon atom number of 1 to 6).

As specific compounds represented by the above general formula [I], for example, following compounds are exemplified.

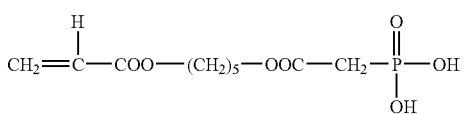

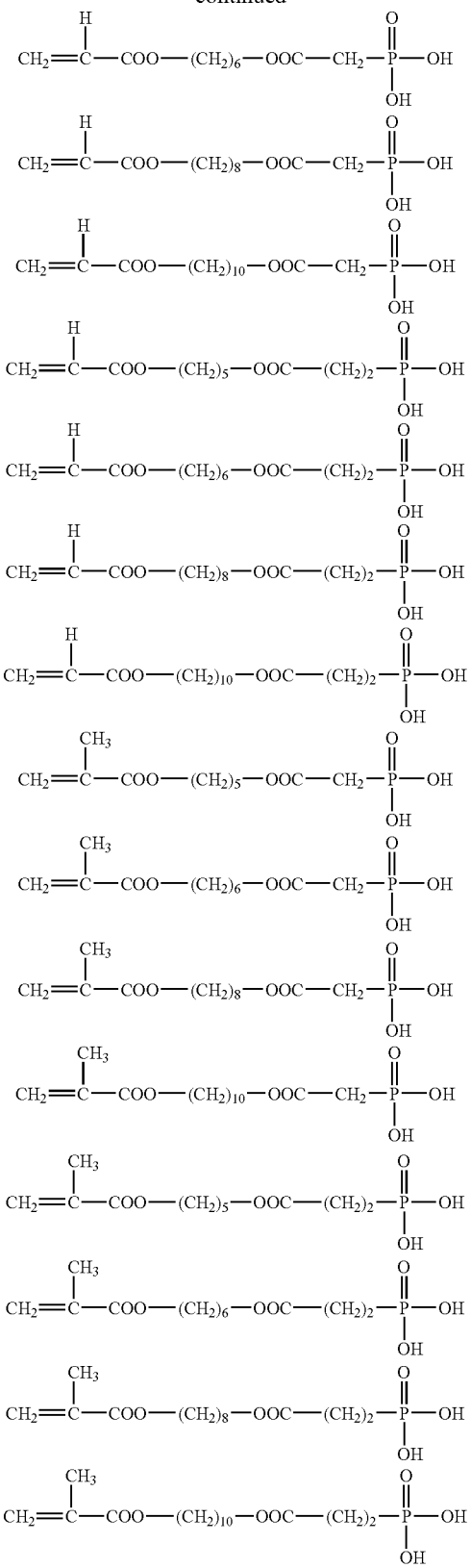

Moreover, as the component (b) used in the resin cement of the present invention, in addition to the compound [I], a polymerizable monomer having a phosphoric acid ester group such as 2-(methacryloxy)ethyl phosphate, bis[2-(methacryloxy)ethyl] phosphate, etc. is also effective.

An amount of the component (b), the polymerizable monomer having a phosphonic acid group and/or a phosphoric acid ester group, used in the resin cement of the present invention is usually 0.05-3.0% by weight, preferably 0.2-3.0% by weight, more preferably 0.3-2.0% by weight based on a total amount of the resin cement of combining two pastes. When the amount is less than 0.05% by weight, then adherability to all of adherents is lowered, whereas when it is greater than 3.0% by weight, then adhesion to dentin is lowered.

Examples of the component (c), a polymerizable monomer having a dibasic acid carboxyl group, used in the resin cement of the present invention include 1,4-di(meth)acryloxyethylpyromellitic acid, 4-(meth)acryloxybutyltrimellitic acid, 4-(meth)acryloxyhexyltrimellitic acid, 4-(meth)acryloxydecyltrimellitic acid, 4-acryloxybutyltrimellitic acid, and 11-(meth)acryloxy-1,1-undecanedicarboxylic acid, etc., and 4-(meth)acryloxyethyltrimellitic acid and 4-(meth)acryloxyethyltrimellitic acid anhydride are particularly preferable.

An amount of the component (c), the polymerizable monomer having a dibasic acid carboxyl group and an acid anhydride residue in the resin cement of the present invention is usually 0.05-5.0% by weight, preferably 0.2-3.0% by weight, and more preferably 0.3-2.0% by weight based on a total amount of the resin cement of combining two pastes. When the amount is less than 0.05% by weight, then adherability to all of adherends is lowered, whereas when it is greater than 5.0% by weight, then a solubility of the polymerizable monomer is lowered.

Examples of the component (d), a filler, used in the resin cement of the present invention include known organic or inorganic fillers and/or organic/inorganic composite fillers, etc.

For example, the known inorganic filler, a fluoroaluminosilicate glass filler may be produced by the known glass production method, and preferably it is produced by a fusion method or a sol-gel method.

The fusion method may include, for example, melting a glass raw material selected from the group consisting of silica, alumina, aluminum hydroxide, aluminum silicate, mullite, calcium silicate, strontium silicate, sodium silicate, sodium carbonate, calcium fluoride, aluminum fluoride, strontium silicate, aluminum phosphate, sodium phosphate, etc. at a high temperature of not lower than 1000° C., followed by cooling and crushing to produce the glass filler.

Following composition is preferable as that of fluoroaluminosilicate glass that may be used in the resin cement of the present invention:

| Calcium oxide | (CaO) | 5~40 mole % |
|---|---|---|
| Silica | ($SiO_2$) | 15~70 mole % |
| Alumina | ($Al_2O_3$) | 10~50 mole % |
| Sodium oxide | ($Na_2O$) | 0~7 mole % |
| Phosphorus pentoxide | ($P_2O_5$) | 0~7 mole % |

An amount of fluorine contained in such the glass is preferably 5 to 60 mole %.

Although calcium oxide is contained in above composition, any alkaline earth metal oxide may be used. At least a part of the alkaline earth metal may be substituted with a lanthanide metal such as lanthanum, gadolinium, ytterbium, etc. Moreover, a part or all of alumina in such the glass may be substituted with III-group metals other than aluminum. In a similar manner, a part of silica in the glass may be substituted with zirconium oxide or titanium oxide. When the glass contains strontium, lanthanum, gadolinium, ytterbium or zirconium, it becomes X-ray opaque.

In addition, the sol-gel method may include, for example, reacting a first solution containing a soluble aluminum compound and a soluble silicon compound with a second solution containing a soluble compound of II-group metals to obtain a gel, and drying the gel by heat drying or freeze drying and collecting it. When this method is used, use of an additive conventionally used for production of glass such as a flux can be avoided, and a relatively low temperature can be used. From this reason, a glass having higher transparency than that of the conventional glass can be obtained.

Moreover, a glass containing a divalent or trivalent metal ion may be obtained by adding other compounds such as an alcohol solution of organic metal salts or inorganic salts in a sol state.

Moreover, an acidic or basic solvent may be added to this sol-gel reaction mixture in order to promote a gelation speed. This method affords a homogeneous fire-resistant glass at a relatively low temperature.

This sol-gel method is particularly suitable for production of a glass into which gadolinium is introduced or a glass consisting of the following five components:

XnOm-CaO—$Al_2O_3$—$SiO_2$—F (wherein, XnOm is an oxide of the X-ray opaque materials, for example, $Gd_2O_3$).

Such a five component glass is difficult to produce. However, the sol-gel method allows for easy manufacturing of such the glass. A CaO source may be replaced by aluminium sec-butoxide in isobutyl alcohol and ethanol, an $SiO_2$ source may be replaced by tetraethyl silicate, an F source may be replaced by 40% hydrofluoric acid, and a $Gd_2O_3$ source may be replaced by ethanol-soluble $Gd(NO_3)_3$ or a methanol solution thereof.

Further, calcium oxide may be replaced by $Ca(NO_3)_2$ anhydride dissolved in ethanol at 50° C. These solutions are mixed at 50° C. by stirring. The mixture may be then refluxed at 70° C. After drying, the obtained material is ground while it is soft and then the ground material is dried at a temperature between 400 to 500° C. Then, this material is further pulverized into a required size.

As the component (d), a filler having an average particle diameter of 0.1 to 10 μm, and preferably 0.1 to 5 μm may be used. In order to improve affinity of the filler for the resin components such as the polymerizable monomer, it is desirable to treat the filler with silane by the conventional method. Examples of a silane treatment agent used include vinyltrimethoxysilane, vinylethoxysilane, vinyltrichlorosilane, γ-methacryloyloxypropyltrimethoxysilane, γ-mercaptopropyltrimethoxysilane, γ-aminopropyltriethoxysilane, etc.

An amount of the component (d), the filler, in the resin cement of the present invention is usually 54.75-80.0% by weight, preferably 57.0-77.0% by weight based on a total amount of the resin cement of combining two pastes. When it is less than 54.75% by weight, then filler settlement or so-called a floating liquid phenomenon may be caused, whereas when it is greater than 80.0% by weight, then fluidity of the paste is significantly reduced to deteriorate cement functions.

The component (e), a polymerizable catalyst, used in the resin cement of the present invention includes a polymerization accelerator ((e)-(1)) and a polymerization initiator ((e)-(2)), and the polymerization initiator includes a chemical polymerization initiator and a photopolymerization initiator.

Among them, the polymerization accelerator may include, for example, an alkali or alkaline earth metal salt of barbituric acid and an aromatic secondary or tertiary amine, etc.

Examples of the alkali or alkaline earth metal salt of barbituric acid include a sodium salt of 5-n-butylbarbituric acid, a calcium salt of 5-n-butylbarbituric acid, a sodium salt of 1-benzyl-5-phenylbarbituric acid, a calcium salt of 1-benzyl-5-phenylbarbituric acid, a sodium salt of 1,3,5-trimethylbarbituric acid, a calcium salt of 1,3,5-trimethylbarbituric acid, etc.

An amount of the component (e)-(1), the alkali or alkaline earth metal salt of barbituric acid, in the resin cement of the present invention is usually 0.025-3.0% by weight, preferably 0.1-2.0% by weight, more preferably 0.7-1.5% by weight based on a total amount of the resin cement of combining two pastes. When it is less than 0.025% by weight, then the curing of the resin cement becomes insufficient, whereas when it is greater than 3.0% by weight, then a suitable manipulating time cannot be obtained since the curing rapidly proceeds.

Examples of the component (e)-(1), the aromatic secondary or tertiary amine, in the resin cement of the present invention include N-dimethylaniline, N-dimethyl-p-toluidine, N,N-di(2-hydroxyethyl)-p-toluidine, and N-methyl-p-toluidine, etc.

An amount of the component (e)-(1), the aromatic secondary or tertiary amine, in the resin cement of the present invention is usually 0.025-1.0% by weight, preferably 0.1-0.8% by weight, and more preferably 0.1-0.5% by weight based on a total amount of the resin cement of combining two pastes. When it is less than 0.025% by weight, then the curing of the resin cement becomes insufficient, whereas when it is greater than 1.0% by weight, then a suitable manipulating time cannot be obtained since the curing rapidly proceeds.

Examples of the chemical polymerization initiator of the compound (e)-(2), the polymerization initiator, in the resin cement of the present invention include an organic peroxide such as benzoyl peroxide, 4,4'-dichlorobenzoyl peroxide, 2,4-dichlorobenzoyl peroxide, dilauryl peroxide, methyl ethyl ketone peroxide, t-butylperoxymaleic acid and peroxysuccinic acid, etc., but t-butylperoxymaleic acid, peroxysuccinic acid and 4,4'-dichlorobenzoyl peroxide are particularly preferable.

Examples of the photopolymerization initiator of the component (e)-(2), the polymerization initiator, in the resin cement of the present invention include an ultraviolet light sensitizer, a visible light sensitizer, etc. such as benzoin methyl ether, benzoin ethyl ether, benzoin isopropyl ether, benzoin, benzophenone, thioxanthon, 2-chlorthioxanthon, 2-hydroxy-3-(3,4-dimethyl-9H-thioxanthen-2-yloxy-N,N,N-trimethyl-1-propane aluminum chloride, 9,10-anthraquinone, camphorquinone, benzil, 4,4'-dicyclobenzil, diacetyl, bis(acyl)phosphine oxides, and mono(acyl)phosphine oxides, etc.

An amount of the component (e)-(2), the polymerization initiator, in the resin cement of the present invention is usually 0.05-2.0% by weight, preferably 0.1-1.5% by weight and more preferably 0.1-1.0% by weight based on a total amount of the resin cement of combining two pastes. When it is less than 0.05% by weight, then the curing of the resin cement becomes insufficient, whereas when it is greater than 2.0% by weight, then a suitable manipulating time cannot be obtained since the curing rapidly proceeds.

The resin cement of the present invention is used by mixing the first paste and the second paste, and the resin cement is cured preferably for 100-600 seconds after mixing two pastes. When the curing time is less than 100 seconds, then a time necessary for manipulating cannot be obtained, whereas when it is greater than 600 seconds, then it greatly gives a burden to a patient.

Examples of the component (f), the shelf life stabilizer, which may be used in the resin cement of the present invention include hydroquinone, hydroquinone monomethyl ether, hydroxymethoxybenzophenone, and butylated hydroxytoluene, etc.

An amount of the component (f), the shelf life stabilizer, in the resin cement of the present invention is usually 0.02-0.2% by weight, and preferably 0.03-0.06% by weight based on a total amount of the resin cement of combining two pastes. When it is less than 0.02% by weight, then a shelf life of the paste becomes insufficient, whereas when it is greater than 0.2% by weight, sufficient curing of the resin cement cannot be obtained.

The resin cement of the present invention is of a two paste-type and consists of a first paste and a second paste. The effect of the resin cement can be exhibited by mixing both of them upon use. A mixing ratio of the first paste and the second paste is, in terms of a weight ratio, usually 1:7-7:1, preferably 1:4-4:1, more preferably 1:2-2:1, and most preferably 1:1.

Since the curing of the resin cement of the present invention is initiated by mixing such the polymerization accelerator ((e)-(1)) and initiator ((e)-(2)), they have to be a separated two paste form until it is used.

Accordingly, when the above component is contained either or both of the first or/and second pastes, the above amount of components which corresponds to the mixing ratio of the first and second pastes, may be contained in the paste.

Therefore, in one embodiment, the present invention provides the aforementioned resin cement, wherein the first paste contains (a) a radical polymerizable monomer, (d) a filler, and (e)-(1) a polymerization accelerator, and the second paste contains (a) a radical polymerizable monomer, (b) a polymerizable monomer having a phosphonic acid group and/or a phosphoric acid ester group, (c) a polymerizable monomer having a dibasic carboxylic acid group, (d) a filler, and (e)-(2) a polymerization initiator.

EXAMPLES

The present invention will be illustrated in detail by the following Examples, but is not limited to such the Examples. Moreover, abbreviation and a method for measuring an adhesive strength described in the Examples are as follows.

[Radical Polymerizable Monomer]

UDMA: Di-2-methacryloyloxyethyl-2,2,4-trimethylhexamethylene dicarbamate

3G: Triethyleneglycol dimethacrylate

Bis-GMA: 2,2'-Bis[4-(3-(meth)acryloyloxy-2-hydroxypropoxy)phenyl]propane

2-HEMA: 2-hydroxyethyl methacrylate [Polymerizable monomer having a phosphonic acid, as represented by the general formula [I]:

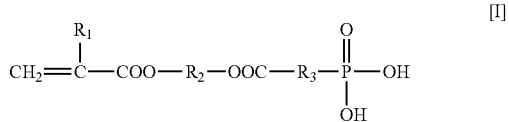

(wherein $R_1$ is a hydrogen atom or a methyl group, $R_2$ represents an alkylene group having the carbon atom number of 5 to 10, and $R_3$ is an alkylene group having the carbon atom number of 1 to 6)]

6-MHPA: (6-Methacryloxy)hexyl phosphonoacetate

The polymerizable monomer represented by the above general formula [I] is produced by the method described in Japanese Patent No. 2865794.

[Polymerizable Monomer having a Phosphoric Acid Ester Group]

2-MEP: 2-(Methacryloxy)ethyl phosphate
Bis-MEP: Bis[2-(methacryloxy)ethyl]phosphate

[Polymerizable Monomer having a Dibasic Acid Carboxyl Group]

4-AET: 4-Acryloxyethyltrimellitic acid
4-MET: 4-Methacryloxyethyltrimellitic acid

[Filler]

FASG filler: Fluoroaluminosilicate glass filler, average particle diameter of 1.8 μm, filler silanated with 8% of γ-methacryloyloxypropyltrimethoxy silane R-711: Ultrafine particle silicafiller

[Polymerization Accelerator]

BBA·Na: Sodium 5-n-butylbarbiturate
BPBA·Ca: Calcium 1-benzyl-5-phenylbarbiturate
DEPT: N,N-di(2hydroxyethyl)-p-toluidine

[Polymerization Initiator]

BPO: Benzoyl peroxide
CQ: Camphorquinone

[Shelf Life Stabilizer]

BHT: Butylated hydroxytoluene (1) Measurement of TG (Thermogravimetry)/DTA (Differential Thermal Analysis):

Measurements were conducted under the following conditions with a thermogravimetric/differential thermal analysis apparatus (Seiko Instruments Inc.).

Sample container: aluminum pan
Rate of nitrogen gas: 200 mL/min
Temperature rising rate: 10° C./min
Reference: alumina (2) Measurement of Adhesive Strength (i) Measurement of Adhesive Strength for Enamel and Dentin A freshly removed bovine anterior tooth was used in stead of a human tooth, and it was embedded in an epoxy resin after removing a part of dental root. A mouth side surface of the tooth was polished with a water-resistant sandpaper under flushing to expose enamel and dentin. The tooth was polished with SiC No. 600, washed with water and air-dried. On the other hand, an adhesive surface of a stainless rod (dia. 4.15 mm), an apparatus for an adhesive test, was sandblast-treated with alumina having a particle diameter of about 50 μm, washed with water and air-dried. A primer for metal materials "METAL LINK" (SHOFU Inc.) was applied to the surface of the stainless rod and it was allowed to dry for 10 seconds. First and second pastes of the resin cement which had been separately filled in double syringes (SULZUR MIXPAC) at an equal amount were kneaded and extruded by passing through an accompanied static mixer. An extruded paste was inserted between the tooth and the stainless rod and they were adhered by applying a 200 g load. An excess paste was removed with a microbrush, light was irradiated along a cement line for 10 seconds. For light irradiation, "Grip Light II" (Shofu Inc.) was used. Ten minutes after light irradiation was finished, the load was removed. The same adhesive test samples (n=6) were immersed in distilled water at 37° C. for 24 hours and then a shear bond strength thereof for the teeth was measured with an Instron type universal tester (Instron 5567, Instron) at 1 mm/min. of a cross head speed.

(ii) Measurement of Adhesive Strength for Porcelain

A one side plane of a fired product of dental porcelain "Vintage Hallow" (Shofu Inc.)(f 11 mm×8.5 mm) was polished with SiC No. 600, washed with water and air-dried. Then the plane was sandblast-treated with alumina having a particle diameter of about 50 μm (0.1-0.2 MPa), washed with water and air-dried. On the other hand, an adhesive surface of a stainless rod (dia. 4.55 mm), an apparatus for an adhesive test, was sandblast-treated with alumina having a particle diameter of about 50 μm, washed with water and air-dried. A primer for metal materials "METAL LINK" (SHOFU Inc.) was applied to the stainless rod and it was allowed to dry spontaneously for 10 seconds and used for measurement. The stainless rod, the apparatus for an adhesive test (dia. 4.55 mm), was used to measure a tensile bond strength for porcelain according to a similar method as that used in (i).

(iii) Measurement of Adhesive Strength for Zirconia

One side plane of flat zirconia (15 mm×15 mm×1.8 mm) (Japan Fine Ceramics Co., Ltd.) was polished with SiC No. 600, washed with water and air-dried. Then the plane was sandblast-treated with alumina having a particle diameter of about 50 μm (0.2-0.3 MPa), washed with water and air-dried. A tensile bond strength for zirconia was measured according to the same method as that used in (ii).

(iv) Measurement of Adhesive Strength for Composite Resins

A metal frame having an inner diameter of 15 mm and a height of 2 mm was placed on a cover glass and a paste of a composite resin "Ceramage" (SHOFU Inc.) was filled therein. The paste of a composite resin was pressed and adhered from both of upper and lower planes through the cover glass, and then either of cover glass planes was upturned and light was irradiated thereto with "Twin Cure" (SHOFU Inc.) for 3 minutes. A bottom plane was sandblast-treated (0.1-0.2 MPa), washed with water and air-dried. A tensile bond strength for the composite resin was measured according to the same method as that used in (ii).

(v) Measurement of Adhesive Strength for Gold Alloys

One side plane of a flat gold alloy "Super Gold 4" (15 mm×15 mm×2.1 mm)(SHOFU Inc.) was polished with SiC No. 600, washed with water and air-dried. Then the plane was sandblast-treated with alumina having a particle diameter of about 50 μm (0.4-0.5 MPa), washed with water and air-dried. A tensile bond strength for the gold alloy was measured according to a similar method as that used in (ii).

(3) Measurement of Curing Times

A curing time of a kneaded mixture of the first and second pastes was measured according to ISO 4049:2000E.

More particularly, 0.8 g of a kneaded paste was filled in a sample well (f4 mm×6 mm) equipped with a thermocouple and an exothermic curve produced by a cure reaction was recorded. The curing time is defined as a time from kneading the pastes to reaching a peak of the exothermic curve, and three measurements were averaged.

Preparation Example 1

Preparation of Sodium 5-n-butylbarbiturate

Into a 100 mL Erlenmeyer flask, was added 25 g of distilled water, and 3.11 g of anhydrous sodium carbonate (29.34 mmol) was added with stirring. It was dissolved in a water bath at 30° C. to obtain an aqueous Na₂CO₃ solution.

Separately, 20 g of distilled water was weighted into a 200 mL beaker, and 10.82 g (58.74 mmol) of 5-n-butylbarbituric acid (BBA) was added to disperse homogeneously to obtain a BBA suspension.

The aqueous Na₂CO₃ solution was added slowly to the BBA suspension, and the mixture was allowed to react for 1 hour in a water bath at 30° C. with stirring. Thereafter, the mixture was concentrated to about 40 g in a water bath at 40-50° C. by an evaporator at 70 cm Hg. About 200 mL of acetone was added to the residue to crystallize it, and solid-liquid separation was conducted by suction filtration. The white crystal obtained was adequately washed with acetone to remove un-reacted BBA, and a remaining crystal was dried under vacuum to obtain a sodium salt of 5-n-butylbarbituric acid (BBA•Na).

A melting point and a decomposition temperature of the obtained salt were measured with thermogravimetry (TG) and differential thermal analysis (DTA). In addition, a pH of a 2% by weight aqueous solution of the obtained salt was measured. Thereby, it was confirmed that a pure salt of barbituric acid was produced.

Preparation Example 2

Preparation of Sodium 1-benzyl-5-phenylbarbiturate

Into a 100 mL Erlenmeyer flask, was added 25 g of distilled water, and 3.11 g of anhydrous sodium carbonate (29.34 mmol) was added with stirring. It was dissolved in a water bath at 30° C. to obtain an aqueous Na₂CO₃ solution.

Separately, 40 g of distilled water and 6 g of acetone were added to a 200 mL beaker, and 17.29 g of 1-benzyl-5-phenyl-barbituric acid (BPBA)(58.74 mmol) was added thereto and the mixture was dispersed homogeneously to obtain an aqueous BPBA/acetone solution.

The aqueous Na₂CO₃ solution was added slowly to the aqueous BPBA/acetone solution, and the mixture was allowed to react for 1 hour in a water bath at about 30° C. with stirring. Thereafter, the mixture was concentrated to about 40 g in a water bath at 40-50° C. by an evaporator at 70 cmHg. About 200 mL of acetone was added to the residue to crystallize it, and solid-liquid separation was conducted by suction filtration. The white crystal obtained was adequately washed with acetone to remove un-reacted BPBA, and a remaining crystal was dried under vacuum to obtain a sodium salt of 1-benzyl-5-phenylbarbituric acid (BPBA•Na).

A melting point and a decomposition temperature of the obtained salt were measured with thermogravimetry (TG) and differential thermal analysis (DTA). In addition, a pH of 2% by weight aqueous solution of the obtained salt was measured. Thereby, it was confirmed that a pure salt of barbituric acid was produced.

Measurement results of above Preparation Examples 1 and 2 are shown in Table 1.

TABLE 1

Melting point, decomposition temperature and pH of barbiturates

|  |  | Melting point (° C.) | Decomposition temperature (° C.) | pH |
|---|---|---|---|---|
| Preparation Example 1 | BBA•Na | — | 377.6 | 7.2 |
| Preparation Example 2 | BPBA•Ca | — | 346.0 | 7.4 |

Example 1

Influences of Composition of Resin Cements on Properties Thereof (1)

(1) Preparation of Resin Cements

Two-paste type resin cements 1-5 consisting of first and second pastes were prepared on a basis of a composition of Table 2. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 2

Composition of resin cements (parts by weight)

| Paste | | Component | 1 | 2 | 3 | 4 | 5 |
|---|---|---|---|---|---|---|---|
| First paste | (a) | UDMA | 10.2 | 10.2 | 10.2 | 10.2 | 10.2 |
| | | 3G | 4.6 | 4.6 | 4.6 | 4.6 | 4.6 |
| | (d) | FASG filler | 33.8 | 33.8 | 33.8 | 33.8 | 33.8 |
| | | R-711 | 1.1 | 1.1 | 1.1 | 1.1 | 1.1 |
| | (e)-(1) | BBA•Na | 0.2 | 0.2 | 0.2 | 0.2 | 0.2 |
| | | DEPT | 0.1 | 0.1 | 0.1 | 0.1 | 0.1 |
| | (f) | BHT | 0.01 | 0.01 | 0.01 | 0.01 | 0.01 |
| Second paste | (a) | Bis-GMA | 8.8 | 8.8 | 8.8 | 8.8 | 8.8 |
| | | 3G | 3.7 | 3.7 | 3.7 | 3.7 | 3.7 |
| | | 2-HEMA | 2.4 | 2.4 | 2.4 | 2.4 | 2.4 |
| | (b) | 2-MEP | — | 2.4 | 1.2 | — | 1.2 |
| | (c) | 4-AET | 2.4 | — | 1.2 | — | — |
| | | 4-MET | — | — | — | 2.4 | 1.2 |
| | (d) | FASG filler | 31.0 | 31.0 | 31.0 | 31.0 | 31.0 |
| | | R-711 | 1.5 | 1.5 | 1.5 | 1.5 | 1.5 |
| | (e)-(2) | BPO | 0.1 | 0.1 | 0.1 | 0.1 | 0.1 |
| | | CQ | 0.1 | 0.1 | 0.1 | 0.1 | 0.1 |
| | (f) | BHT | 0.03 | 0.03 | 0.03 | 0.03 | 0.03 |

(2) Evaluation of Properties of Resin Cements

[Adhesive Strength]

A shear bond strength for the tooth sample (enamel and dentin) and a tensile bond strength for each sample of zirconia, porcelain, a composite resin and a gold alloy of the resin cements 1-5 were measured. The measurement results are shown in Table 3.

TABLE 3

Evaluation of properties of resin cements

| Item | | 1 | 2 | 3 | 4 | 5 |
|---|---|---|---|---|---|---|
| Shear bond strength (MPa) Average (SD) | Enamel | 16.7 (3.5) | 8.5 (3.3) | 24.5 (5.4) | 18.0 (4.7) | 17.2 (3.2) |
| | Dentin | 5.8 (2.2) | 6.1 (2.1) | 6.5 (1.9) | 8.8 (2.0) | 7.3 (2.6) |
| Tensile bond strength (MPa) Average (SD) | Zirconia | 13.2 (1.9) | 15.0 (2.2) | 14.6 (4.0) | 15.2 (3.2) | 18.5 (2.6) |
| | Porcelain | 10.2 (2.7) | 8.3 (3.4) | 10.2 (2.9) | 9.1 (2.4) | 8.1 (2.1) |
| | Composite resin | 13.3 (2.7) | 8.7 (2.7) | 9.4 (2.9) | 10.2 (2.6) | 8.9 (2.3) |
| | Gold alloy | 17.4 (3.4) | 17.2 (3.6) | 16.5 (2.5) | 18.4 (2.2) | 18.9 (2.8) |

The resin cement 1 contains 4-AET as a component (c), but not a component (b) The resin cement 2 contains no component (c), but contains 2-MEP as a component (b). And, the resin cement 3 contains both components (c) and (b) (4-AET and 2-MEP). In this case, a significant synergistic effect in an adhesive strength for enamel was observed in a combination of the components (c) and (b).

Example 2

Influences of Composition of Resin Cements on Properties Thereof (2)

(1) Preparation of Resin Cements

Two-paste type resin cements 6-10 consisting of first and second pastes were prepared on a basis of a composition of Table 4. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 4

Composition of resin cements (parts by weight)

| Paste | | Component | 6 | 7 | 8 | 9 | 10 |
|---|---|---|---|---|---|---|---|
| First paste | (a) | UDMA | 10.2 | 10.2 | 10.2 | 10.2 | 10.2 |
| | | 3G | 4.6 | 4.6 | 4.6 | 4.6 | 4.6 |
| | (d) | FASG filler | 33.8 | 33.8 | 33.8 | 33.8 | 33.8 |
| | | R-711 | 1.1 | 1.1 | 1.1 | 1.1 | 1.1 |
| | (e)-(1) | BBA·Na | 0.2 | 0.2 | 0.2 | 0.2 | 0.2 |
| | | DEPT | 0.1 | 0.1 | 0.1 | 0.1 | 0.1 |
| | (f) | BHT | 0.01 | 0.01 | 0.01 | 0.01 | 0.01 |
| Second paste | (a) | Bis-GMA | 8.8 | 8.8 | 8.8 | 8.8 | 8.8 |
| | | 3G | 3.7 | 3.7 | 3.7 | 3.7 | 3.7 |
| | | 2-HEMA | 2.4 | 2.4 | 2.4 | 2.4 | 2.4 |
| | (b) | Bis-MEP | — | 2.4 | 1.2 | — | 1.2 |
| | (c) | 4-AET | 2.4 | — | 1.2 | — | — |
| | | 4-MET | — | — | — | 2.4 | 1.2 |
| | (d) | FASG filler | 31.0 | 31.0 | 31.0 | 31.0 | 31.0 |
| | | R-711 | 1.5 | 1.5 | 1.5 | 1.5 | 1.5 |
| | (e)-(2) | BPO | 0.1 | 0.1 | 0.1 | 0.1 | 0.1 |
| | | CQ | 0.1 | 0.1 | 0.1 | 0.1 | 0.1 |
| | (f) | BHT | 0.03 | 0.03 | 0.03 | 0.03 | 0.03 |

(2) Evaluation of Properties of Resin Cements
[Adhesive Strength]

A shear bond strength for the tooth sample (enamel and dentin) and a tensile bond strength for each sample of zirconia, porcelain, a composite resin and a gold alloy of the resin cements 6-10 were measured. The measurement results are shown in Table 5.

TABLE 5

Evaluation of properties of resin cements

| Item | | 6 | 7 | 8 | 9 | 10 |
|---|---|---|---|---|---|---|
| Shear bond strength (MPa) Average (SD) | Enamel | 16.7 (3.5) | 14.5 (1.2) | 24.5 (5.4) | 18.0 (4.7) | 26.0 (3.9) |
| | Dentin | 5.8 (2.2) | 3.8 (1.3) | 6.8 (1.2) | 8.8 (2.0) | 8.4 (2.8) |
| Tensile bond strength (MPa) Average (SD) | zirconia | 13.2 (1.9) | 16.6 (4.3) | 13.3 (3.0) | 15.2 (3.2) | 13.3 (1.6) |
| | Porcelain | 10.2 (2.7) | 6.4 (1.9) | 11.0 (2.7) | 9.1 (2.4) | 8.6 (2.8) |
| | Composite resin | 13.3 (2.7) | 8.5 (4.3) | 9.5 (2.2) | 10.2 (2.6) | 10.3 (3.9) |
| | Gold alloy | 17.4 (3.4) | 18.2 (3.2) | 16.3 (2.2) | 18.4 (2.2) | 17.8 (4.4) |

The resin cement 6 contains 4-AET as the component (c), but not the component (b). The resin cement 7 contains no component (c), but contains Bis-MEP as the component (b). And, the resin cement 8 contains both components (c) and (b) (4-AET and Bis-MEP). In this case, a significant synergistic effect in an adhesive strength for enamel was observed in a combination of the components (c) and (b).

Similarly, the resin cement 9 contains 4-MET as the component (c), but not the component (b). The resin cement 6 contains no component (c), but contains Bis-MEP as the component (b). And, the resin cement 10 contains both components (c) and (b) (4-MET and Bis-MEP). Also in this case, a significant synergistic effect in an adhesive strength for enamel was observed in a combination of the components (c) and (b).

Example 3

Influences of Composition of Resin Cements on Properties Thereof (3)

(1) Preparation of Resin Cements

Two-paste type resin cements 11-15 consisting of first and second pastes were prepared on a basis of a composition of Table 6. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 6

Composition of resin cements (parts by weight)

| Paste | | Component | 11 | 12 | 13 | 14 | 15 |
|---|---|---|---|---|---|---|---|
| First paste | (a) | UDMA | 10.2 | 10.2 | 10.2 | 10.2 | 10.2 |
| | | 3G | 4.6 | 4.6 | 4.6 | 4.6 | 4.6 |
| | (d) | FASG filler | 33.8 | 33.8 | 33.8 | 33.8 | 33.8 |
| | | R-711 | 1.1 | 1.1 | 1.1 | 1.1 | 1.1 |
| | (e)-(1) | BBA·Na | 0.2 | 0.2 | 0.2 | 0.2 | 0.2 |
| | | DEPT | 0.1 | 0.1 | 0.1 | 0.1 | 0.1 |
| | (f) | BHT | 0.01 | 0.01 | 0.01 | 0.01 | 0.01 |
| Second paste | (a) | Bis-GMA | 8.8 | 8.8 | 8.8 | 8.8 | 8.8 |
| | | 3G | 3.7 | 3.7 | 3.7 | 3.7 | 3.7 |
| | | 2-HEMA | 2.4 | 2.4 | 2.4 | 2.4 | 2.4 |
| | (b) | 6-MHPA | — | 2.4 | 1.2 | — | 1.2 |
| | (c) | 4-AET | 2.4 | — | 1.2 | — | — |
| | | 4-MET | — | — | — | 2.4 | 1.2 |
| | (d) | FASG filler | 31.0 | 31.0 | 31.0 | 31.0 | 31.0 |
| | | R-711 | 1.5 | 1.5 | 1.5 | 1.5 | 1.5 |
| | (e)-(2) | BPO | 0.1 | 0.1 | 0.1 | 0.1 | 0.1 |
| | | CQ | 0.1 | 0.1 | 0.1 | 0.1 | 0.1 |
| | (f) | BHT | 0.03 | 0.03 | 0.03 | 0.03 | 0.03 |

(2) Evaluation of Properties of Resin Cements
[Adhesive Strength]

A shear bond strength for the tooth sample (enamel and dentin) and a tensile bond strength for each sample of zirconia, porcelain, a composite resin and gold alloy of the resin cements 11-15 were measured. The measurement results are shown in Table 7.

TABLE 7

Evaluation of properties of resin cements

| Item | | 11 | 12 | 13 | 14 | 15 |
|---|---|---|---|---|---|---|
| Shear bond strength (MPa) Average (SD) | Enamel | 16.7 (3.5) | 22.5 (5.4) | 18.8 (4.8) | 18.0 (4.7) | 28.8 (2.0) |
| | Dentin | 5.8 (2.2) | 11.5 (3.4) | 15.0 (3.1) | 8.8 (2.0) | 16.5 (4.3) |
| Tensile bond strength (MPa) Average (SD) | Zirconia | 13.2 (1.9) | 15.3 (2.0) | 16.8 (2.3) | 15.2 (3.2) | 16.5 (2.2) |
| | Porcelain | 10.2 (2.7) | 11.0 (1.8) | 11.0 (1.4) | 9.1 (2.4) | 8.2 (1.7) |
| | Composite resin | 13.3 (2.7) | 7.8 (2.3) | 8.9 (1.7) | 10.2 (2.6) | 8.3 (1.7) |
| | Gold alloy | 17.4 (3.4) | 12.0 (2.7) | 17.3 (2.0) | 18.4 (2.2) | 19.0 (2.2) |

The resin cement 11 contains 4-AET as the component (c), but not the component (b). The resin cement 12 contains no component (c), but contains 6-MHPA as the component (b). And, the resin cement 13 contains both components (c) and (b). (4-AET and 6-MHPA). In this case, a significant synergistic effect in an adhesive strength for dentin was observed in a combination of the components (c) and (b).

Similarly, the resin cement 14 contains 4-MET as the component (c), but not the component (b). The resin cement 12 contains no component (c), but contains 6-MHPA as the component (b). And, the resin cement 15 contains both components (c) and (b) (4-MET and 6-MHPA). In this case, a significant synergistic effect in an adhesive strength for enamel and dentin was observed in a combination of the components (c) and (b).

Example 4

Influences of Composition of Resin Cements on Properties Thereof (4)

(1) Preparation of Resin Cements

Two-paste type resin cements 16-21 consisting of first and second pastes were prepared on a basis of a composition of Table 8. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 8

Composition of resin cements (parts by weight)

| Paste | | Component | 16 | 17 | 18 | 19 | 20 | 21 |
|---|---|---|---|---|---|---|---|---|
| First paste | (a) | Bis-GMA | 10.5 | 10.5 | 10.5 | 10.5 | 10.5 | 10.5 |
| | | 3G | 5.0 | 5.0 | 5.0 | 5.0 | 5.0 | 5.0 |
| | (d) | FASG filler | 33.3 | 33.2 | 33.1 | 32.8 | 32.3 | 31.3 |
| | | R-711 | 1.0 | 1.0 | 1.0 | 1.0 | 1.0 | 1.0 |
| | (e)-(1) | BPBA•Ca | — | 0.1 | 0.2 | 0.5 | 1.0 | 2.0 |
| | | DEPT | 0.2 | 0.2 | 0.2 | 0.2 | 0.2 | 0.2 |
| | (f) | BHT | 0.01 | 0.01 | 0.01 | 0.01 | 0.01 | 0.01 |
| Second paste | (a) | UDMA | 8.8 | 8.8 | 8.8 | 8.8 | 8.8 | 8.8 |
| | | 3G | 3.7 | 3.7 | 3.7 | 3.7 | 3.7 | 3.7 |
| | | 2-HEMA | 2.4 | 2.4 | 2.4 | 2.4 | 2.4 | 2.4 |
| | (b) | 6-MHPA | 1.2 | 1.2 | 1.2 | 1.2 | 1.2 | 1.2 |
| | (c) | 4-AET | 1.2 | 1.2 | 1.2 | 1.2 | 1.2 | 1.2 |
| | (d) | FASG filler | 31.0 | 31.0 | 31.0 | 31.0 | 31.0 | 31.0 |
| | | R-711 | 1.5 | 1.5 | 1.5 | 1.5 | 1.5 | 1.5 |
| | (e)-(2) | BPO | 0.1 | 0.1 | 0.1 | 0.1 | 0.1 | 0.1 |
| | | CQ | 0.1 | 0.1 | 0.1 | 0.1 | 0.1 | 0.1 |
| | (f) | BHT | 0.03 | 0.03 | 0.03 | 0.03 | 0.03 | 0.03 |

(2) Evaluation of Properties of Resin Cements

[Adhesive Strength]

A shear bond strength for the tooth sample (enamel and dentin) and a tensile bond strength for each sample of zirconia, porcelain, a composite resin and a gold alloy of the resin cements 16-21 were measured. The measurement results are shown in Table 9.

[Curing Time]

The curing time of the resin cements 16-21 were measured. The measurement results are shown in Table 9.

TABLE 9

Evaluation of properties of resin cements

| | | Resin cement | | | | | |
|---|---|---|---|---|---|---|---|
| Item | | 16 | 17 | 18 | 19 | 20 | 21 |
| Shear bond strength (MPa) Average (SD) | Enamel | 6.0 (2.1) | 19.7 (3.5) | 19.9 (3.2) | 21.3 (4.1) | 17.5 (2.7) | 20.0 (3.2) |
| | Dentin | 6.9 (1.1) | 14.3 (2.8) | 11.5 (1.8) | 14.6 (2.8) | 14.1 (2.5) | 6.3 (0.8) |
| Tensile bond strength (MPa) Average (SD) | Zirconia | 7.8 (1.3) | 16.3 (2.8) | 24.4 (1.4) | 16.4 (1.5) | 26.8 (3.7) | 24.9 (4.4) |
| | Porcelain | 5.7 (0.8) | 11.2 (1.6) | 24.5 (3.0) | 20.0 (3.1) | 24.9 (3.0) | 15.7 (3.2) |
| | composite resin | 5.2 (0.9) | 14.1 (2.5) | 12.5 (2.1) | 13.4 (1.8) | 15.3 (2.9) | 13.2 (1.9) |
| | Gold alloy | 6.3 (0.7) | 17.8 (2.2) | 21.3 (3.0) | 18.4 (1.6) | 22.4 (2.1) | 22.7 (3.8) |
| Curing time (second) | | 642 | 393 | 294 | 278 | 266 | 225 |

From evaluation of properties of the resin cement 16, it was found that lack of the component (e)-(1), a salt of barbituric acid, results in a lowered adhesive strength and an extended curing time of the resin cement.

Moreover, comparing the resin cements 17 to 21, it was found that all of the resin cements have a suitable adhesive strength and a suitable curing time.

Thereby, it was confirmed that an optimal content of the component (e)-(1), a salt of barbituric acid, is 0.1-2.0 parts by weight.

Example 5

Influences of Composition of Resin Cements on Properties Thereof (5)

(1) Preparation of Resin Cements

Two-paste type resin cements 22-27 consisting of first and second pastes were prepared on a basis of a composition of Table 10. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 10

Composition of resin cements (parts by weight)

| Paste | | Component | 22 | 23 | 24 | 25 | 26 | 27 |
|---|---|---|---|---|---|---|---|---|
| First paste | (a) | Bis-GMA | 10.5 | 10.5 | 10.5 | 10.5 | 10.5 | 10.5 |
| | | 3G | 5.0 | 5.0 | 5.0 | 5.0 | 5.0 | 5.0 |
| | (d) | FASG filler | 33.3 | 33.2 | 33.1 | 32.8 | 32.3 | 31.3 |
| | | R-711 | 1.0 | 1.0 | 1.0 | 1.0 | 1.0 | 1.0 |
| | (e)-(1) | BPBA•Ca | 0.2 | 0.2 | 0.2 | 0.2 | 0.2 | 0.2 |
| | | DEPT | — | 0.1 | 0.2 | 0.5 | 1.0 | 2.0 |
| | (f) | BHT | 0.01 | 0.01 | 0.01 | 0.01 | 0.01 | 0.01 |
| Second paste | (a) | UDMA | 8.8 | 8.8 | 8.8 | 8.8 | 8.8 | 8.8 |
| | | 3G | 3.7 | 3.7 | 3.7 | 3.7 | 3.7 | 3.7 |
| | | 2-HEMA | 2.4 | 2.4 | 2.4 | 2.4 | 2.4 | 2.4 |
| | (b) | 6-MHPA | 1.2 | 1.2 | 1.2 | 1.2 | 1.2 | 1.2 |
| | (c) | 4-AET | 1.2 | 1.2 | 1.2 | 1.2 | 1.2 | 1.2 |
| | (d) | FASG filler | 31.0 | 31.0 | 31.0 | 31.0 | 31.0 | 31.0 |
| | | R-711 | 1.5 | 1.5 | 1.5 | 1.5 | 1.5 | 1.5 |
| | (e)-(2) | BPO | 0.1 | 0.1 | 0.1 | 0.1 | 0.1 | 0.1 |
| | | CQ | 0.1 | 0.1 | 0.1 | 0.1 | 0.1 | 0.1 |
| | (f) | BHT | 0.03 | 0.03 | 0.03 | 0.03 | 0.03 | 0.03 |

(2) Evaluation of Properties of Resin Cements

[Adhesive Strength]

A shear bond strength for the tooth sample (enamel and dentin) and a tensile bond strength for each sample of zirconia, porcelain, a composite resin and a gold alloy of the resin cements 22-27 were measured. The measurement results are shown in Table 11.

[Curing Time]

The curing time of the resin cements 22-27 were measured. The measurement results are shown in Table 11.

TABLE 11

Evaluation of properties of resin cements

| | | Resin cement | | | | | |
|---|---|---|---|---|---|---|---|
| Item | | 22 | 23 | 24 | 25 | 26 | 27 |
| Shear bond | Enamel | 11.6 (3.5) | 13.0 (2.2) | 14.5 (3.5) | 16.7 (1.9) | 8.6 (3.3) | — |
| strength (MPa) Average (SD) | Dentin | 7.8 (1.0) | 10.0 (2.3) | 11.6 (2.8) | 10.5 (1.2) | 4.2 (1.8) | — |
| Tensile bond strength (MPa) Average (SD) | Zirconia | 11.5 (3.1) | 15.8 (2.8) | 26.9 (3.8) | 18.3 (1.1) | — | — |
| | Porcelain | 4.1 (2.7) | 15.9 (2.8) | 22.7 (4.2) | 19.9 (2.9) | — | — |
| | Composite resin | 3.0 (0.7) | 12.8 (2.4) | 13.0 (1.8) | 16.1 (2.2) | — | — |
| | Gold alloy | 6.3 (1.2) | 15.8 (2.2) | 15.2 (3.2) | 20.2 (3.6) | — | — |
| Curing time (second) | | not less than 1200 | 430 | 231 | 105 | 77 | 20 |

From evaluation of properties of the resin cement 22, it was found that lack of the component (e)-(1), amine, results in a lowered adhesive strength and a significantly extended curing time of the resin cement.

Moreover, comparing the resin cements 23 to 27, it was found that a greater amount of the component (e)-(1), an amine, results in a shorter curing time and an insufficient adhesive manipulating ability.

Furthermore, the resin cement 26 had a shorter curing time and an insufficient adhesive manipulating ability. In addition, in the resin cement 27, measurement data of an adhesive strength and the curing time could not be obtained since it had a shorter curing time.

Thereby, it was confirmed that an optimal content of the component (e)-(1), an amine, is 0.1-0.5 parts by weight.

Example 6

Influences of Composition of Resin Cements on Properties Thereof (6)

(1) Preparation of Resin Cements

Two-paste type resin cements 28-33 consisting of first and second pastes were prepared on a basis of a composition of Table 12. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 12

Composition of resin cements (parts by weight)

| Paste | | Component | 28 | 29 | 30 | 31 | 32 | 33 |
|---|---|---|---|---|---|---|---|---|
| First paste | (a) | Bis-GMA | 10.4 | 10.4 | 10.4 | 10.4 | 10.4 | 10.4 |
| | | 3G | 5.0 | 5.0 | 5.0 | 5.0 | 5.0 | 5.0 |
| | (d) | FASG filler | 33.1 | 33.2 | 33.2 | 33.2 | 33.2 | 33.2 |
| | | R-711 | 1.0 | 1.0 | 1.0 | 1.0 | 1.0 | 1.0 |
| | (e)-(1) | BPBA•Ca | 0.2 | 0.2 | 0.2 | 0.2 | 0.2 | 0.2 |
| | | DEPT | 0.2 | 0.2 | 0.2 | 0.2 | 0.2 | 0.2 |
| | (f) | BHT | 0.01 | 0.01 | 0.01 | 0.01 | 0.01 | 0.01 |
| Second paste | (a) | UDMA | 8.8 | 8.8 | 8.8 | 8.8 | 8.8 | 8.8 |
| | | 3G | 3.7 | 3.7 | 3.7 | 3.7 | 3.7 | 3.7 |
| | | 2-HEMA | 2.4 | 2.4 | 2.4 | 2.4 | 2.4 | 2.4 |

TABLE 12-continued

Composition of resin cements (parts by weight)

| Paste | | Component | 28 | 29 | 30 | 31 | 32 | 33 |
|---|---|---|---|---|---|---|---|---|
| | (b) | 6-MHPA | 1.2 | 1.2 | 1.2 | 1.2 | 1.2 | 1.2 |
| | (c) | 4-AET | 1.2 | 1.2 | 1.2 | 1.2 | 1.2 | 1.2 |
| | (d) | FASG filler | 31.1 | 31.0 | 30.9 | 30.6 | 30.4 | 30.1 |
| | | R-711 | 1.5 | 1.5 | 1.5 | 1.5 | 1.5 | 1.5 |
| (e)-(2) | | BPO | — | 0.1 | 0.2 | 0.5 | 0.7 | 1.0 |
| | | CQ | 0.1 | 0.1 | 0.1 | 0.1 | 0.1 | 0.1 |
| (f) | | BHT | 0.03 | 0.03 | 0.03 | 0.03 | 0.03 | 0.03 |

(2) Evaluation of Properties of Resin Cements

[Adhesive Strength]

A shear bond strength for the tooth sample (enamel and dentin) and a tensile bond strength for each sample of zirconia, porcelain, a composite resin and a gold alloy of the resin cements 28-33 were measured. The measurement results are shown in Table 13.

[Curing Time]

The curing time of the resin cements 28-33 were measured. The measurement results are shown in Table 13.

TABLE 13

Evaluation of properties of resin cements

| | | Resin cement | | | | | |
|---|---|---|---|---|---|---|---|
| Item | | 28 | 29 | 30 | 31 | 32 | 33 |
| Shear bond strength (MPa) Average (SD) | Enamel | 11.2 (3.5) | 22.8 (3.5) | 26.3 (4.2) | 24.1 (3.9) | 26.7 (5.1) | 30.1 (4.5) |
| | Dentin | 3.0 (1.3) | 4.7 (1.2) | 16.4 (2.8) | 17.6 (3.2) | 19.6 (2.1) | 9.6 (2.8) |
| Tensile bond strength (MPa) Average (SD) | Zirconia | 22.0 (2.7) | 18.4 (2.7) | 17.4 (2.6) | 24.4 (1.4) | 18.9 (2.6) | 18.4 (1.8) |
| | Porcelain | 10.7 (3.4) | 14.5 (2.8) | 13.8 (1.2) | 18.0 (3.3) | 21.3 (2.2) | 24.8 (2.7) |
| | Composite resin | 5.2 (0.4) | 16.6 (2.7) | 15.9 (1.5) | 15.1 (2.1) | 14.2 (2.3) | 14.6 (1.6) |
| | Gold alloy | 12.5 (1.1) | 14.8 (3.4) | 18.2 (1.1) | 20.1 (2.5) | 22.1 (4.0) | 20.3 (1.6) |
| Curing time (second) | | not less than 1200 | 498 | 383 | 286 | 252 | 182 |

From evaluation of properties of the resin cement 28, it was found that lack of the component (e)-(2), organic peroxide, results in a lowered adhesive strength and a significantly extended curing time.

Thereby, it was confirmed that an optimal content of the component (e)-(2), organic peroxide, is 0.1-1.0 parts by weight.

Example 7

Influences of Composition of Resin Cements on Properties Thereof (7)

(1) Preparation of Resin Cements

Two-paste type resin cements 34-38 consisting of first and second pastes were prepared on a basis of a composition of Table 14. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 14

Composition of resin cements (parts by weight)

| Paste | | Component | 34 | 35 | 36 | 37 | 38 |
|---|---|---|---|---|---|---|---|
| First paste | (a) | Bis-GMA | 10.5 | 10.5 | 10.5 | 10.5 | 10.5 |
| | | 3G | 5.0 | 5.0 | 5.0 | 5.0 | 5.0 |
| | (d) | FASG filler | 33.2 | 33.2 | 33.2 | 33.2 | 33.2 |
| | | R-711 | 1.0 | 1.0 | 1.0 | 1.0 | 1.0 |
| | (e)-(1) | BPBA·Ca | 0.1 | 0.1 | 0.1 | 0.1 | 0.1 |
| | | DEPT | 0.2 | 0.2 | 0.2 | 0.2 | 0.2 |
| | (f) | BHT | 0.01 | 0.01 | 0.01 | 0.01 | 0.01 |
| Second paste | (a) | UDMA | 9.5 | 9.5 | 9.5 | 9.5 | 9.5 |
| | | 3G | 5.2 | 4.9 | 4.4 | 3.4 | 2.4 |
| | | 2-HEMA | 1.2 | 1.2 | 1.2 | 1.2 | 1.2 |
| | (b) | 6-MHPA | 0.2 | 0.5 | 1.0 | 2.0 | 3.0 |
| | (c) | 4-AET | 1.2 | 1.2 | 1.2 | 1.2 | 1.2 |

TABLE 14-continued

Composition of resin cements (parts by weight)

| Paste | | Component | 34 | 35 | 36 | 37 | 38 |
|---|---|---|---|---|---|---|---|
| | (d) | FASG filler | 31.0 | 31.0 | 31.0 | 31.0 | 31.0 |
| | | R-711 | 1.5 | 1.5 | 1.5 | 1.5 | 1.5 |
| | (e)-(2) | BPO | 0.1 | 0.1 | 0.1 | 0.1 | 0.1 |
| | | CQ | 0.1 | 0.1 | 0.1 | 0.1 | 0.1 |
| | (f) | BHT | 0.03 | 0.03 | 0.03 | 0.03 | 0.03 |

(2) Evaluation of Properties of Resin Cements

[Adhesive Strength]

A shear bond strength for the tooth sample (enamel and dentin) and a tensile bond strength for each sample of zirconia, porcelain, a composite resin and a gold alloy of the resin cements 34-38 were measured. The measurement results are shown in Table 15.

TABLE 15

Evaluation of properties of resin cements

| Item | | Resin cement | | | | |
|---|---|---|---|---|---|---|
| | | 34 | 32 | 33 | 34 | 38 |
| Shear bond strength (MPa) Average (SD) | Enamel | 19.4 (3.1) | 18.5 (3.5) | 19.8 (3.1) | 24.5 (1.9) | 16.2 (2.5) |
| | Dentin | 11.5 (2.0) | 16.1 (1.6) | 23.0 (3.2) | 19.9 (2.6) | 15.0 (2.5) |
| Tensile bond Strength (MPa) Average (SD) | Zirconia | 18.5 (1.4) | 23.9 (3.2) | 20.3 (2.4) | 25.6 (2.8) | 21.5 (1.8) |
| | Porcelain | 15.1 (3.0) | 16.9 (1.7) | 17.6 (1.2) | 19.2 (1.9) | 17.8 (2.2) |
| | Composite resin | 14.8 (1.6) | 15.3 (0.8) | 12.9 (1.8) | 16.0 (1.3) | 15.2 (1.9) |
| | Gold alloy | 16.5 (3.3) | 16.1 (1.5) | 15.7 (0.8) | 15.2 (1.5) | 17.1 (2.8) |

By comparing the resin cements 34 to 38, it was found that a sufficient adhesive strength can be obtained in a content of 0.2-3.0 parts by weight of the component (b), a polymerizable monomer having a phosphonic acid group and/or a phosphoric acid ester group.

Thereby, it was confirmed that a proper content of the component (b), a polymerizable monomer having a phosphonic acid group and/or a phosphoric acid ester group, is 0.2-3.0 parts by weight.

Example 8

Influences of Composition of Resin Cements on Properties Thereof (8)

(1) Preparation of Resin Cements

Two-paste type resin cements 39-43 consisting of first and second pastes were prepared on a basis of a composition of Table 16. In this Example, a total amount of components in each of the first and second pastes other than the component (f), a shelf life stabilizer, was made to be 50 parts by weight based on a total amount of the resin cement composition, and a proper amount of the component (f) was added to each of the pastes.

TABLE 16

Composition of resin cements (parts by weight)

| Paste | | Component | 39 | 40 | 41 | 42 | 43 |
|---|---|---|---|---|---|---|---|
| First paste | (a) | Bis-GMA | 10.5 | 10.5 | 10.5 | 10.5 | 10.5 |
| | | 3G | 5.0 | 5.0 | 5.0 | 5.0 | 5.0 |
| | (d) | FASG filler | 33.2 | 33.2 | 33.2 | 33.2 | 33.2 |
| | | R-711 | 1.0 | 1.0 | 1.0 | 1.0 | 1.0 |
| | (e)-(1) | BPBA•Ca | 0.1 | 0.1 | 0.1 | 0.1 | 0.1 |
| | | DEPT | 0.2 | 0.2 | 0.2 | 0.2 | 0.2 |
| | (f) | BHT | 0.01 | 0.01 | 0.01 | 0.01 | 0.01 |
| Second paste | (a) | UDMA | 9.9 | 9.9 | 9.9 | 9.9 | 9.9 |
| | | 3G | 5.8 | 5.2 | 4.2 | 2.2 | 0.2 |
| | | 2-HEMA | 0.2 | 0.5 | 1.0 | 2.0 | 3.0 |
| | (b) | 6-MHPA | 1.2 | 1.2 | 1.2 | 1.2 | 1.2 |
| | (c) | 4-AET | 0.2 | 0.5 | 1.0 | 2.0 | 3.0 |
| | (d) | FASG filler | 31.0 | 31.0 | 31.0 | 31.0 | 31.0 |
| | | R-711 | 1.5 | 1.5 | 1.5 | 1.5 | 1.5 |

TABLE 16-continued

Composition of resin cements (parts by weight)

| Paste | | Component | 39 | 40 | 41 | 42 | 43 |
|---|---|---|---|---|---|---|---|
| | (e)-(2) | BPO | 0.1 | 0.1 | 0.1 | 0.1 | 0.1 |
| | | CQ | 0.1 | 0.1 | 0.1 | 0.1 | 0.1 |
| | (f) | BHT | 0.03 | 0.03 | 0.03 | 0.03 | 0.03 |

(2) Evaluation of Properties of Resin Cements
[Adhesive Strength]

A shear bond strength for the tooth sample (enamel and dentin) and a tensile bond strength for each sample of zirconia, porcelain, a composite resin and a gold alloy of the resin cements 39-43 were measured. The measurement results are shown in Table 17.

TABLE 17

Evaluation of properties of resin cements

| Item | | Resin cement | | | | |
|---|---|---|---|---|---|---|
| | | 39 | 40 | 41 | 42 | 43 |
| Shear bond strength (MPa) Average (SD) | Enamel | 15.2 (2.2) | 21.8 (2.2) | 21.4 (2.2) | 28.9 (2.6) | 33.2 (1.4) |
| | Dentin | 14.1 (3.0) | 17.2 (2.9) | 17.7 (2.5) | 17.5 (3.3) | 21.0 (1.8) |
| Tensile bond strength (MPa) Average (SD) | Zirconia | 21.9 (3.5) | 24.2 (3.1) | 21.4 (2.2) | 25.4 (2.1) | 28.2 (2.0) |
| | Porcelain | 21.4 (3.3) | 21.3 (3.1) | 21.6 (2.6) | 20.5 (2.6) | 26.0 (2.1) |
| | Composite resin | 16.6 (1.2) | 16.0 (1.4) | 17.8 (1.9) | 16.7 (2.5) | 14.8 (2.3) |
| | Gold alloy | 18.2 (1.4) | 16.7 (1.2) | 20.1 (2.3) | 19.9 (2.2) | 18.0 (0.8) |

By comparing the resin cements 39 to 43, it was found that a sufficient adhesive strength can be obtained in a content of 0.2-3.0 parts by weight of the component (c), a polymerizable monomer having a dibasic carboxylic acid group.

Thereby, it was confirmed that a proper content of the component (c), a polymerizable monomer having a dibasic carboxylic acid group, is 0.2-3.0 parts by weight.

INDUSTRIAL APPLICABILITY

According to the present invention, there can be provided a dental material having an excellent adhesive strength, without treatment with a primer corresponding to various adherends.

What is claimed is:

1. A two-paste type dental self-adhesive composite resin cement consisting of a first paste and a second paste, which exhibits an effective shear bond strength for dentin,
wherein, the first paste comprises, on a basis of 50% by weight of the first paste:
(a)-(1) 8.0-22.5% by weight of a radical polymerizable monomer,
(d)-(1) 27.45-40.0% by weight of a filler, and
(e)-(1) 0.025-1.0% by weight of an alkali metal salt or an alkaline earth metal salt of barbituric acid and/or 0.025-0.5% by weight of aromatic secondary or tertiary amine, and
the second paste comprises, on a basis of 50% by weight of the second paste:
(a)-(2) 5.0-22.5% by weight of a second radical polymerizable monomer, (b) 0.05-3.0% by weight of a polymerizable monomer having a phosphonic acid group represented by formula [I]:

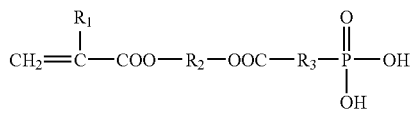

wherein $R_1$ is a hydrogen atom or a methyl group, $R_2$ is an alkylene group of the carbon atom number of 5-10, and $R_3$ is an alkylene group of the carbon atom number 1-6, (c) 0.05-3.0% by weight of a polymerizable monomer having a dibasic acid carboxyl group, (d)-(2) 27.3-40.0% by weight of a second filler, and (e)-(2) 0.3-0.8% by weight of a chemical polymerization initiator and/or a photopolymerization initiator, and wherein both of the pastes are free from water.

* * * * *